(12) United States Patent
Busetti et al.

(10) Patent No.: US 10,143,715 B2
(45) Date of Patent: Dec. 4, 2018

(54) COMPOSITION FOR THE PREVENTION AND/OR TREATMENT OF ALLERGY SYMPTOMS

(71) Applicant: NTC S.R.L., Milan (IT)

(72) Inventors: Cesare Busetti, Milan (IT); Fabrizio Niccolai, Milan (IT); Daniela Zelaschi, Milan (IT)

(73) Assignee: NTC S.R.L., Milan (IT)

(*) Notice: Subject to any disclaimer, the term of this patent is extended or adjusted under 35 U.S.C. 154(b) by 0 days.

(21) Appl. No.: 15/504,117

(22) PCT Filed: Sep. 21, 2015

(86) PCT No.: PCT/IB2015/057267
§ 371 (c)(1),
(2) Date: Feb. 15, 2017

(87) PCT Pub. No.: WO2016/046728
PCT Pub. Date: Mar. 31, 2016

(65) Prior Publication Data
US 2017/0258864 A1  Sep. 14, 2017

(30) Foreign Application Priority Data
Sep. 22, 2014 (IT) .............. MI2014A1641

(51) Int. Cl.
| | |
|---|---|
| *A61K 36/535* | (2006.01) |
| *A61K 9/20* | (2006.01) |
| *A23L 33/105* | (2016.01) |
| *A61K 9/48* | (2006.01) |
| *A61K 31/592* | (2006.01) |
| *A61K 31/352* | (2006.01) |
| *A61K 31/192* | (2006.01) |
| *A61K 9/24* | (2006.01) |
| *A61K 31/216* | (2006.01) |
| *A61K 31/353* | (2006.01) |
| *A61K 31/593* | (2006.01) |

(52) U.S. Cl.
CPC .......... *A61K 36/535* (2013.01); *A23L 33/105* (2016.08); *A61K 9/209* (2013.01); *A61K 9/2013* (2013.01); *A61K 9/48* (2013.01); *A61K 9/4808* (2013.01); *A61K 31/192* (2013.01); *A61K 31/216* (2013.01); *A61K 31/352* (2013.01); *A61K 31/353* (2013.01); *A61K 31/593* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2008/0070875 A1* | 3/2008 | Majewski | A61K 31/60 514/161 |
| 2011/0111055 A1 | 5/2011 | Lang | |
| 2012/0020902 A1 | 1/2012 | Giuliani et al. | |

FOREIGN PATENT DOCUMENTS

JP   2001114686 A   4/2001

OTHER PUBLICATIONS

Search Report and Written Opinion of PCT/IB2015/057267 dated Jan. 28, 2016.
Takano H., et al., "Extract of Perilla Frutescens enriched for rosmarinic acid, a polyphenolic phytochemical, inhibits seasonal allergic rhinoconjunctivitis in humans", Experimental Biology and Medicine, Society for Experimental Biology and Medicine, US vol. 229, No. 3, Mar. 1, 2004, pp. 247-254.

\* cited by examiner

Primary Examiner — Michael Barker
(74) Attorney, Agent, or Firm — Silvia Salvadori, P.C.; Silvia Salvadori

(57) ABSTRACT

The present invention relates to a pharmaceutical composition or a food supplement composition and use thereof in the prevention and/or treatment of allergy symptoms, preferably allergic rhinitis and/or allergic conjunctivitis symptoms. In particular, the composition according to the invention comprises at least one slow release component comprising quercetin and at least one fast release component comprising an extract from *Perilla frutescens* or a constituent thereof selected from luteolin, rosmarinic acid, apigenin, catechina, ferulic acid, caffeic acid or mixtures thereof, The invention further comprises the use of the composition in the prevention and/or treatment of allergy symptoms, preferably allergic rhinitis and/or allergic conjunctivitis symptoms.

16 Claims, 2 Drawing Sheets

COMPOSITION FOR THE PREVENTION AND/OR TREATMENT OF ALLERGY SYMPTOMS

This application is a U.S. national stage of PCT/IB2015/057267 filed on 21 Sep. 2015, which claims priority to and the benefit of Italian Application No. MI2014A001641 filed on 22 Sep. 2014, the contents of which are incorporated herein by reference in their entireties.

The present invention relates to a pharmaceutical composition or a food supplement composition and use thereof in the prevention and/or treatment of allergy symptoms, preferably allergic rhinitis and/or allergic conjunctivitis symptoms.

As known, allergies are caused by an immune system response to a class of substances known as allergens, which generally do not generate disorders in most of people. The manifestation of the allergic phenomenon occurs in two sequential steps: a first step of sensitization and a second step wherein the real allergic reaction occurs. During the sensitization step, the immune system recognizes and memorizes the allergen, with the resulting production of immunoglobulin E (IgE), specific for each allergen. IgEs quickly pass into the blood where they fix on the mast cell surface. In the second step the real allergic reaction occurs, during which the contact between the allergen and the sensitized organism occurs. The bond between IgEs and the allergen causes mast cell degranulation, with the resulting release of histamine and lipid mediators, such as leukotrienes and prostaglandins. Once histamine achieves the sites of the specific receptors, for example those one located in the nasal mucosa or conjunctiva, it triggers allergy symptoms, such as sneezing, itching and red eyes.

To this end, the use of antihistamines against the histamine action is known. Particularly, quercetin, which belongs to the flavonol class, represents the aglyconic part of several glycosides and it is considered a natural antihistamine capable to block the recruitment, the activation and the degranulation of mast cells. Advantageously, quercetin does not cause the common side effects of slackness and drowsiness caused by other antihistamines.

Similarly, great interest is aroused by the extracts from the plant *Perilla frutescens*, as said extracts contain several functional components, among which aglycones of flavonoids, such as luteolin, apigenin and rosmarinic acid, which are provided with inhibitory activity against the release of interleukins, leukotrienes and cytokines from mast cells and basophils. In fact, some cell studies have shown as *perilla* extracts have an inhibitory activity on the degranulation and histamine release from mast cells, as well as blocking the 5-lipoxygenase enzyme activity, which is involved in the production of inflammation intermediates. Further studies showed that *perilla* extracts inhibit IgEs production and reduce the grade of asthma severity.

It is known from several studies that quercetin bioavailability increases with a lipid-enriched diet (S. Lesser et al., British Journal of Nutrition (2006), 96, 1047-1052).

The oral administration of active ingredients occurs always considering the physiological processes of absorption and excretion.

Currently, several types of formulations for the release of active ingredients are available; tablets, capsules and sachets or stick packs are preferred forms for the oral administration. Such formulations may be made, so as to allow the release and adsorption of the active ingredient at different levels of the gastrointestinal tract, according to the desired absorption kinetic.

WO 01/28526 discloses a delayed-release formulation of active ingredients, preferably in the form of tablet, comprising at least one active ingredient and a hydrogenated fatty acid. Therefore it deals with a slow release formulation over time, so as the active ingredient to be released from the formulation by imitating the physiological conditions of the digestive process, which normally occurs in the stomach.

In view of the above, it is evident the need to have a pharmaceutical composition or a food supplement composition for the prevention and/or treatment of allergy symptoms, preferably allergic rhinitis and/or allergic conjunctivitis symptoms, which enhances the absorption of the active ingredients contained in the composition itself.

The Applicant has now found that such technical problem is solved by a composition as following defined, wherein quercetin is combined with an extract from *Perilla frutescens* or a constituent thereof selected from luteolin, rosmarinic acid, apigenin, catechin, ferulic acid, caffeic acid or mixtures thereof, wherein quercetin is inserted in a slow release component, instead the extract from *Perilla frutescens* (hereinafter "*perilla*"), namely at least one constituent thereof as above defined, is inserted in a fast release component. Thereby, the absorption of the two different active ingredients occurs in differentiated tracts of the gastrointestinal tract, so as to enhance the action of both.

Therefore, according to a first embodiment, the present invention relates to a composition comprising:
- at least one slow release component comprising quercetin; and
- at least one fast release component comprising an extract from *Perilla frutescens* or a constituent thereof selected from luteolin, rosmarinic acid, apigenin, catechin, ferulic acid, caffeic acid or mixture thereof.

Advantageously, according to a preferred embodiment of the present invention, the above-mentioned composition is in the form of tablet, and even more preferably in the form of bilayer tablet, wherein one layer is a slow release layer and the other layer is a fast release layer. The composition of the invention imitates the fat absorption in the gastrointestinal tract and it simultaneously allows the absorption of active ingredients contained in the composition itself to be enhanced. This effect is particularly evident in the embodiment as tablet, preferably in the form of layer, and even more preferably bilayer.

A further advantage of the preferred embodiment is represented in that the composition of the present invention allows to take advantage of the different properties of the two components, particularly of the layers which form the bilayer composition, with the resulting selective release of the active ingredients. That corresponds to an increase of effectiveness against allergy symptoms with respect to the known compositions used in said treatments. This result depends on both the features of the components and the ingredients of the composition according to the invention.

The composition according to the invention, as well as preventing and/or treating the symptoms of the allergy reaction, is particularly useful also in reducing the amount of other active pharmaceutically ingredients commonly used for the treatment of allergy symptoms. For example, in the case of patients already treated with other antiallergic drugs, the composition of the invention allows to reduce the administered amounts of said other drugs thus limiting the side effects of the latter such as, for example, drowsiness, incoordination, vision alteration and digestive disorders of the anticholinergic type. Therefore, the composition according to the invention represents an excellent tool against allergic manifestations, preferably characterized by rhinitis and conjunctivitis, due to pollen seasonal allergy. Furthermore, the absence of side effects were demonstrated, both when the association of the active ingredients quercetin and *perilla* is administered alone, and when it is administered in conjunction with other drugs, such as antiallergic drugs.

Further features and advantages of the present invention will be evident from the following detailed description.

As far as quercetin is concerned, it is incorporated into the slow release component which prolong its dissolution over time, also increasing the bioavailability and therefore the therapeutic effectiveness. That allows both postponing the release into the bowel, and facilitating the absorption into the bowel itself, thanks to the formation in situ of a micelle structure.

Quercetin derives from a natural or synthetic source. When quercetin derives from a natural source, it preferably derives from *Sophora Japonica* or *Dimorphandra mollis*, more preferably *Sophora Japonica*. According to another preferred embodiment, quercetin is in the form of its glucosides and/or salts thereof, more preferably quercetin is quercetin dihydrated. Preferably, quercetin is in a percentage from 1% to 70%, preferably from 3% to 60%, more preferably from 5% to 50%, where each % is referred to the total weight of the composition.

According to a preferred embodiment, quercetin is in the composition in a quantity from 50 mg to 1000 mg, preferably from 75 mg to 500 mg, more preferably from 100 mg to 500 mg.

The slow release component may comprise cholecalciferol (vitamin D3), preferably in an amount from 1 µg to 10 µg.

As far as the extract from *Perilla frutescens* is concerned, said extract is preferably hydrosoluble. Preferably, the extract from *Perilla frutescens* has a high content of flavonoids, luteolin and apigenin, in particular the total content of apigenin and luteolin is preferably comprised between 0.001% by weight and 2% by weight, more preferably comprised between 0.01% by weight and 1% by weight, where the percentages by weight are referred to the total weight of the extract. Preferably, said extract derives from leafs or seeds of *Perilla frutescens*, more preferably seeds of *Perilla frutescens*.

According to another preferred embodiment of the invention, said extract is a dry extract. It is also possible to use a liquid extract, particularly in the case in which products in the liquid or gel form are intended to be made.

According to another preferred embodiment, the composition of the invention comprises an amount of *perilla* extract from 5 mg to 500 mg, more preferably from 25 mg to 300 mg, even more preferably from 50 mg to 300 mg.

Preferably said *perilla* extract is in a percentage from 1% to 50%, more preferably from 2% to 40%, even more preferably from 3% to 30%, where each % is referred to the total weight of the composition.

According to a preferred embodiment, the slow release component (or slow release layer) comprises a fat-soluble compound, preferably selected from fatty acids $C_8$-$C_{24}$, glycerides, fatty alcohol $C_8$-$C_{24}$, or mixture thereof, which act as retardant agents and/or absorption promoters.

The preferred fatty acids are the saturated $C_{12}$-$C_{18}$ fatty acids, unsaturated, hydrogenated or mixture thereof, more preferably selected from lauric acid ($C_{12}$) (e.g., commercially available as Neo-Fat 12), miristic acid ($C_{14}$), palmitic acid ($C_{16}$), stearic acid ($C_{18}$), linoleic acid ($C_{18}$) (e.g., commercially available as Emersol 310) or mixture thereof.

The preferred glycerides are mono-, di-, tri-glycerides (for example, acylglycerols $C_8$-$C_{22}$), more preferably selected from hydrogenated castor oil (for example, Cutin HR), hydrogenated vegetal oil (for example, commercially available as Lubritab), glyceryl behenate (for example, commercially available as Compritol E), glyceryl monostearate (for example, commercially available as Imwitor 900), PEG-15 hydroxystearate (for example, commercially available as Solutol HS 15), vegetable stearin or mixture thereof, even more preferably vegetable stearin.

Preferred aliphatic alcohols which may be comprised in the slow release component are $C_{12}$-$C_{18}$ alcohols, more preferably selected from cetyl alcohol (for example, commercially available as Codacol C70), cetostearilic alcohol (for example, commercially available as Lanette O), stearyl alcohol (for example, commercially available as Crodacol S95) or mixture thereof.

According to another embodiment of the invention, the slow release component may further comprise at least one fat-soluble vitamin, preferably Vitamin E TPGS (d-alpha tocopheryl polyethylene glycol 1000 succinate), and/or at least one surfactant, preferably a surfactant with HLB comprised between 8 and 18.

Preferred surfactants that may be comprised in the slow release component are lecitin (for example, commercially available as Epikuron, Lipoid), sucroesters (for example, commercially available as Ryoto Sucrose Esters S-1570), POE-POP copolymers (for example, commercially available as Pluronic), polyoxyethylenglycole esters (for example, commercially available as Gelucire 44/14) or mixture thereof.

The fast release component of the compositions according to the present invention may comprise disintegrating agents, excipient diluents, adjuvants, lubricants (flux agents), sweeteners or mixture thereof.

Presumably, the fast release component dissolves in the stomach and it is adsorbed mainly in the small intestine.

In order to obtain a differentiated release of the several active ingredients, the two components, both solid, must be separated at macroscopic or microscopic level. For example, in the first case, each of the two components may form one layer of the bilayer tablet, or each component may be made in the form of minitablets, which are mixed within a capsule. Alternatively, the two components may be prepared separately, for example in the form of granulate, and then associated each other resulting in this way indistinguishable at macroscopic level, for example by simple mixing of the two granulates which are packed in sachets, or the mixture of the two granulates may be used for making monolayer tablets.

In any case, quercetin is inglobated in the slow release component separately from the fast release component, where the extract from *Perilla frutescens* or a constituent thereof as above defined is inglobated.

In the present description and in the enclosed claims, the expression "fast release component" means a component, separated from the slow release component, which is capable to completely disintegrate in water, at the temperature of 37° C., in a time not higher than 10 minutes, preferably not higher than 5 minutes, more preferably not higher than 2 minutes.

In the present description and in the enclosed claims, the expression "slow release component" means a component, separated from the fast release component, which is capable to completely disintegrate in water, at the temperature 37° C., in a time not lower than 1 hour, preferably not lower than 2 hours, more preferably not lower than 3 hours.

In both cases, the disintegration time is determined according to the method described in the European Pharmacopoeia (5$^{th}$ edition), "2.9.1. "Disintegration of tablets and capsules", pag. 225-227.

Preferred disintegrating agents are cornstarch, sodium starch glycolate, croscarmellose sodium (for example, commercially available as Ac-di-Sol), crospovidon, preferably cross-linked polyvinylpirrolidone (for example, commercially available as Kollidon CL), sodium carboxymethyl starch, soy polysaccharide (for example, commercially available as Emcosoy) and mixture thereof. Preferred excipient diluents are starch, for example, cornstarch, rice starch and/or wheat, pregelatinized starch, lactose monohydrate, lactose DC, mannitol (for example, commercially available as Pearlitol), sorbitol, calcium phosphate dibasic anhydrous or dyhydrate (for example, commercially available as Emcompress), calcium phosphate tribasic, calcium carbonate DC (for example, commercially available as PharMagnesia CC Type 140), microcrystalline cellulose (for example, commercially available as Avicel), hydroxypropylcellulose (for example, commercially available as Klucel), hydroxypropyl cellulose with low degree of substitution (L-HPC), sodium carboxymethylcellulose (for example, commercially available as Blanose), powdered cellulose (for example, commercially available as Arbocel), dextrates (for example, commercially available as Emdex), saccharose DC (for example, commercially available as Comprizucker), isomaltose (for example, commercially available as Isomaltidex 16500), maltodextrin (for example, commercially available as Glucidex) or mixture thereof, preferably microcrystalline cellulose and/or maltodextrin.

Preferred adjuvants are commercially available and are, for example, Prosolv EasyTab, namely a mixture of microcrystalline cellulose, colloidal silicon dioxide, sodium starch glycolate, sodium stearyl fumarate, Prosolv SMCC, namely silicified microcrystalline cellulose, Cellactose 80, namely a mixture of co-processed lactose and cellulose, Starlac, namely a mixture of co-processed lactose and starch, Microcelac, namely a mixture of lactose and microcrystalline cellulose, Lycatab Mineral, namely a mixture of co-processed calcium carbonate and starch or mixture thereof.

Preferred lubricants or flux agents are colloidal anhydrous silica (for example, commercially available as Aerosil), hydrated colloidal silica (for example, commercially available as Sipernat), talc magnesium stearate, calcium stearate, stearic acid, sodium stearyl fumarate (for example, commercially available as PRUV) or mixture thereof, preferably magnesium stearate.

Preferred sweeteners are sodium saccharin, acesulfame potassium, aspartame, sodium cyclamate, sucralose, stevia, thaumatin or mixture thereof.

According to a preferred embodiment, the composition according to the invention may comprise one or more natural, synthetic or artificial aromas.

According to another preferred embodiment, the composition object of the invention further comprises a filming component. Preferably said filming layer comprises ethyl cellulose, talc, carnauba wax or mixture thereof. Advantageously, the filming allow to avoid the dust formation during packing operations and the production of not perfectly sealed blisters.

According to a preferred embodiment, the composition of the invention may be in the form of tablets, capsules, sachets or granulate for oral administration, more preferably in the form of tablets.

According to a second embodiment, the present invention relates to the composition as above defined for use in the prevention and/or treatment of allergy symptoms, preferably allergic rhinitis and/or allergic conjunctivitis symptoms.

According to a third embodiment, the present invention relates to the composition as above defined for use as food supplement.

BRIEF DESCRIPTION OF THE DRAWINGS

The present invention will be now described, for illustrative, but not limitative purposes, according to its preferred embodiments, with particular reference to the figures of the enclosed drawings, wherein.

EXAMPLE 1

Figure 1:
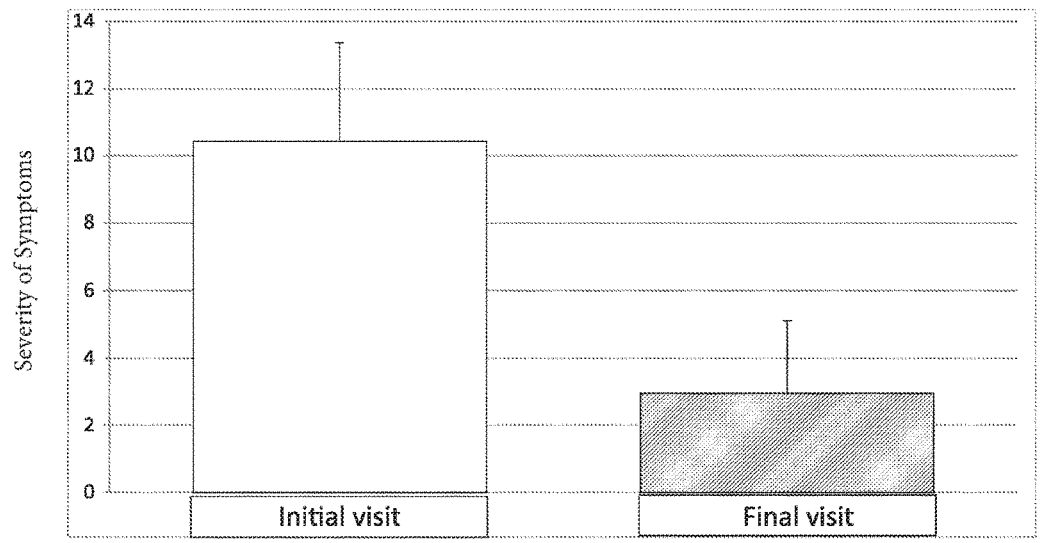
FIG. 1 shows data related to total average reduction of symptoms (±DS), obtained by comparing the severity of symptoms found at the initial and final visit after the administration of a composition according to the invention, as reported in the experimentation of example 1.
Figure 2:
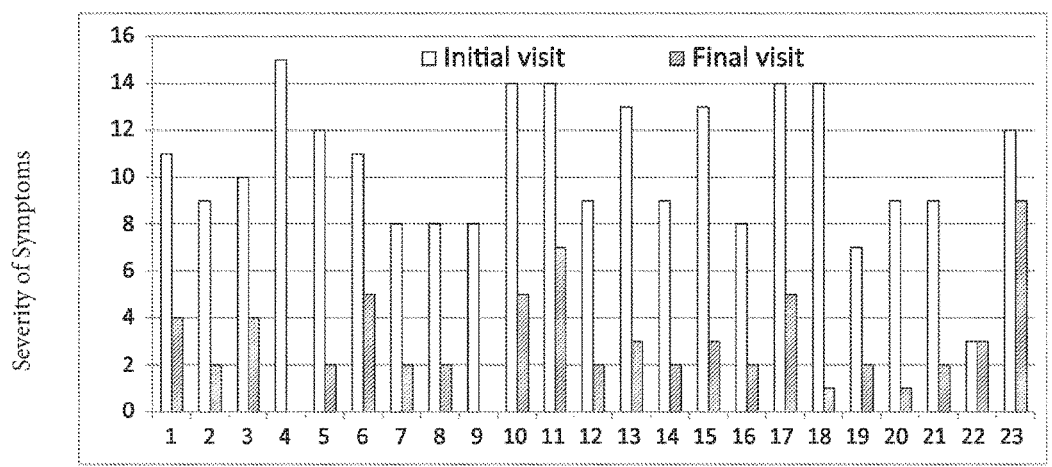
FIG. 2 shows data related to the reduction of the total score of symptoms for each patient obtained by comparing the results obtained at the initial and final visit after the administration of a composition according to the invention, as reported in the experimentation of example 1.

A clinical trial was carried out in order to demonstrate the effectiveness of the composition of the invention in reducing the nasal and ocular symptoms in the allergic subjects involved. Similarly, the effect of the intake of the composition on the consumption of other anti-allergy drugs was assessed.

The subjects involved in the trial were 23 adult, namely 16 women with an average age of 44 years old and 7 men, with an average age of 46 years old. All the subjects had a story of allergic rhinitis and/or conjunctivitis for at least one year and were positive to the prick test or RAST for *Parietaria officinalis* pollen. The subjects, at the moment of the involvement in the trial, have all the nasal and/or ocular symptoms of the seasonal allergic rhinitis.

Subjects suffering from bacterial or viral infections of the upper or lower respiratory tracts, paranasal sinuses or ear, within the thirty days before their involvement in the trial, were excluded from the trial. Similarly, pregnant women or women during nursing or women that intended to start a pregnancy within the period of the trial, were excluded.

The experimentation was carried out according to a open clinical trial by administering the composition of the invention, as reported in the example 2, in the form of tablet, twice daily (morning and evening), during or after meals, for 30 consecutive days. After having carried out the two daily administrations, patients reported symptoms by filling in an assessment sheet which included six parameters, namely sneezing, Rinorrea, nasal obstruction, ocular itching, lachrymation, congestion of conjunctiva, according to a numeric score ranging from 0 to 3 (rating scale: 0=no episode; 1=1-5 episodes/day, 2=6-10 episodes/days; 3=≥11 episodes/day). Patients were subjected to a total of two clinical visits (initial visit, before starting the trial and final visit, at the end of the trial) carried out one month away (the treatment duration was of about 30 days). Particularly, during the first visit, the following information for each patient were collected: demographic details, clinical history, with particular reference to the onset of the ongoing allergic pathology, the assessment of nasal and/or ocular symptoms, the assessment of the consumption of anti-allergic drugs, the inclusion or exclusion criteria, concomitant intake of other drugs, with possible side effects, as well as the informed consent request. Instead, during the second visit the following information were assessed: the assessment of the severity of the nasal and/or ocular symptoms reached during the period of drug administration, the assessment of the consumption of anti-allergic drugs and possible side effects reached during the administration period of the composition according to the invention. Simultaneously, it was carried out the monitoring of *Parietaria Officinalis* allergens into the atmosphere of Imperia district, where the trial was carried out, for the entire duration of the trial.

Results

Figure 3:
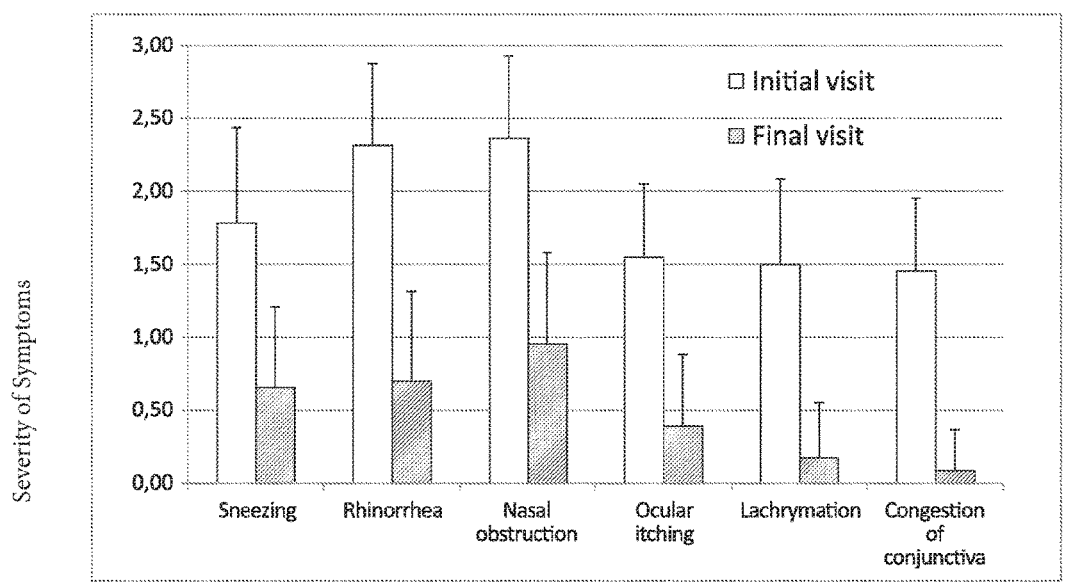
FIG. 3 shows data related to the reduction of the different symptoms individually considered, by comparing the results obtained at the initial and final visit after the administration of a composition according to the invention, as reported in the experimentation of example 1.

The comparison between the scores obtained from the two visits (initial and final) simultaneously shows an average reduction of about 70% for the symptomatological scores and of about 73% as far as the consumption of other anti-allergic drugs is concerned. In FIGS. 1 and 3 are reported, respectively, the data related to the total average reduction of symptoms and the reduction of the several symptoms individually considered, always comparing the results obtained in the first and second visit.

Particularly, by comparing the results obtained for both sexes (see Table 1) it is evident the same trend, with results slightly better for women (less 72% of symptoms and less 76% of consumption of other drugs) with respect to the results obtained for men (less 68% of symptoms and less 67% of consumption of other drugs).

TABLE 1

(average values)

|  | Women (n = 16) | Men (n = 7) |
| --- | --- | --- |
| Age (years) | 44 | 46 |
| Symptomps reduction | 72% | 68% |
| Consumption reduction of anti-allergic drugs | 76% | 67% |

None of the subjects had relevant side effect and none of the subjects interrupted the treatment before of the thirty days expected.

In the period considered, the level of *Parietaria* allergens into the atmosphere was always high, as weekly monitored by reading of Urticaceae levels in the regional pollen bulletin, station of Imperia, published on-line on the ARPAL (REGIONAL AGENCY FOR THE LIGURIAN ENVIRONMENT PROTECTION) website.

EXAMPLE 2

Below an example of the preparation of a composition according to the invention, in the form of bilayer tablet, namely comprising both the fast release component and the slow release component in two separated layers, is reported.

The amounts of the ingredients used in the following preparation process are indicated in Table 2, reported below.

According to the process carried out, quercetin and vitamin $D_3$ were mixed with fused stearin obtaining a granulate cooled at room temperature (20-25° C.). After cooling, the granulate was made uniform by means of a sieve.

Microcrystalline cellulose, silicon dioxide and magnesium stearate have been added to the granulate and the whole was mixed until obtaining an homogeneous granulate. Said preparation represents the slow release component (or layer).

The ingredients of the fast release component (or layer), namely dry extract of *perilla* seeds, cross-linked sodium carboxymethylcellulose (cross-linked CMC Na), maltodextrin, microcrystalline cellulose, silicon dioxide and magnesium stearate, were mixed until obtaining an homogeneous mixture.

The granulate (slow release component) and the mixture (fast release component or layer) separately feed the loading stations of a tableting machine suitable to form bilayer tablets.

Tablets with a 9 mm diameter were obtained, formed by two distinct layers, characterized by a different dissolution profile. Tablets were then protected by a filming layer consisting of methylcellulose, talc and carnauba wax.

TABLE 2

| Ingredient | Amount |
| --- | --- |
| Slow release component | |
| Quercetin | 150.0 mg |
| Vitamin D3 | 5.0 µg |
| Vegetable stearin | 35.0 mg |
| Microcrystalline cellulose | 30.0 mg |
| Silicon dioxide | 1.5 mg |
| Mg stearate | 2.0 mg |
| Fast release component | |
| *Perilla* seeds (hydrosoluble dry extract) | 80.0 mg |
| Cross-linked CMC Na | 3.0 mg |
| Maltodextrin | 40.0 mg |
| Microcrystalline cellulose | 18.5 mg |
| Silicom dioxide | 0.8 mg |
| Magnesium stearate | 1.8 mg |
| Filming component | |
| Ethyl cellulose | 2.0 mg |
| Talc | 1.0 mg |
| Carnauba wax | 0.2 mg |

Tablets thus obtained were subjected to a disintegration test in water, at the temperature of 37° C., according to what is described in the European Pharmacopoeia ($5^{th}$ edition), "2.9.1. "Disintegration of tablets and capsules", pag. 225-227. The first layer, consisting of the fast release component, disintegrated in less than 2 minutes, instead the second layer, consisting of the slow release component, disintegrated in about 3 hours and 50 minutes.

EXAMPLE 3

Below an example of the preparation of a composition according to the invention, in the form of monolayer tablet, is reported.

The amounts of the ingredients used in the following preparation process are indicated in Table 3, reported below.

According to the process carried out, quercetin, vitamin $D_3$ and microcrystalline cellulose were mixed and kneaded with fused glyceryl behenate. After cooling, the granulate were made uniform by means of a sieve.

All the other ingredients were added to the granulate. After mixing, tablets of a weight of 450 mg were manufactured. Tablets then were filmed with a filming layer consisting of methylcellulose, talc and carnauba wax.

TABLE 3

| Ingredient | Amount |
| --- | --- |
| Quercetin | 150.0 mg |
| Perilla seeds (hydrosoluble dry extract) | 80.0 mg |
| Vitamin D3 | 5.0 µg |
| Glyceryl behenate | 50.0 mg |
| Maltodextrin | 80.0 mg |
| Microcrystalline cellulose | 70.0 mg |
| Sodium starch glycolate | 13.0 mg |
| Stearic acid | 4.6 mg |
| Filming component | |
| Ethylcellulose | 2.0 mg |
| Talc | 1.0 mg |
| Carnauba wax | 0.2 mg |

EXAMPLE 4

Below an example of the preparation of a composition according to the invention, in the form of sachet, is reported.

The amounts of the ingredients used in the following preparation process are indicated in Table 4, reported below.

According to the process carried out, quercetin, vitamin D₃ and maltodextrin were mixed and kneaded with polyoxyethylenglicol esters (Gelucire 44/14) (melted) obtaining a granulate. After cooling, the granulate was made uniform by means of a sieve.

All the other components were added to the granulate, mixed until obtaining an homogeneous preparation. The mixture was dosed in sachets of a weight of 3 g/sachet.

TABLE 4

| Ingredient | Amounts |
| --- | --- |
| Quercetin | 200.0 mg |
| Perilla seeds (hydrosoluble dry extract) | 100.0 mg |
| Vitamin D3 | 5.0 µg |
| Gelucire 44/14 | 200.0 mg |
| Sucroester P1570 | 100.0 mg |
| Maltodextrin | 500.0 mg |
| Mannite | 2000.0 mg |
| Fructose | 1832.6 mg |
| Sodium saccharin | 15.0 mg |
| Aroma | 50.0 mg |

EXAMPLE 5

Below an example of the preparation of a composition according to the invention, in the form of capsule, is reported.

The amounts of the ingredients used in the following preparation process are indicated in Table 5, reported below.

According to the process carried out, quercetin, vitamin D3 were mixed with microcrystalline cellulose and kneaded with melted hydrogenated fatty acids. After cooling, the granulate was made uniform by means of a sieve. Maltodextrin, silicon dioxide and magnesium stearate were added to the calibrated granulate, with subsequent mixing until obtaining a homogeneous preparation. The granulate was compressed by lenticular punches of 2 mm diameter obtaining minitablets of about 20 mg by weight (slow release minitablets).

The components of the fast release minitablets (Perilla seeds dry extract, maltodextrin, HPC, silicon dioxide, magnesium stearate) were mixed until obtaining an homogeneous preparation. The mixture was compressed by lenticular punches of 2 mm diameter obtaining minitablets of about 20 mg by weight (fast release minitablets).

About 15 slow release minitablets and about 8 fast release minitablets were dosed, by a suitable automatic encapsulator, in capsules of HPMC (hydroxypropylmethylcellulose) format 1.

TABLE 5

| Ingredient | Amount |
| --- | --- |
| Slow release minitablets | |
| Quercetin | 150.0 mg |
| Vitamin D3 | 5.0 µg |
| Hydrogenated fatty acids | 40.0 mg |
| Microcrystalline cellulose | 30.0 mg |
| Maltodextrin | 71.5 mg |
| Silicon dioxide | 1.5 mg |
| Mg stearate | 2.0 mg |
| Fast release minitablets | |
| Perilla seeds (hydrosoluble dry extract) | 80.0 mg |
| Maltodextrin | 61.4 mg |
| Hydroxypropylcellulose | 10.0 mg |
| Sodium Croscarmellose | 6.0 mg |
| Silicon dioxide | 0.8 mg |
| Magnesium stearate | 1.8 mg |

EXAMPLE 6

Below it is reported a pilot micro-study carried out on a patient with known allergy to birch pollens and strong symptomatology both nasal and ocular, which normally needs of topic pharmacological treatment (nasal-spray and/or eye drops) and/or systemic. Following the weekly pollen calendar, the product according to Example 2 was administered to the patient with the increase of the pollen count, even under the limits which cause symptomatology. The patient never had any symptoms nor took any type of anti-allergic drug as deduced by the daily calendar.

The invention claimed is:

1. Method of preventing and/or treating allergy symptoms in a subject in need thereof with a composition comprising:
    at least one slow release component comprising quercetin; and
    at least one fast release component comprising an extract from *Perilla frutescens* or a constituent thereof selected from luteolin, rosmarinic acid, apigenin, catechin, ferulic acid, caffeic acid or mixture thereof, said method comprising:
    administering to said subject an effective amount of said composition, wherein said allergy symptoms comprise allergic rhinitis and/or allergic conjunctivitis symptoms.

2. The method according to claim 1, wherein quercetin is in the form of its glucosides and/or its salts.

3. The method according to claim 1, wherein quercetin derives from *Sophora Japonica* or *Dimorphandra mollis*.

4. The method according to claim 1, wherein quercetin is in a percentage from 1% to 70%, where each % is referred to the total weight of the composition.

5. The method according to claim 1, wherein quercetin is in the composition in an amount from 50 mg to 1000 mg.

6. The method according to claim 1, wherein the *perilla frutescens* extract is water-soluble.

7. The method according to claim 1, wherein the *perilla frutescens* extract derives from leafs or seeds of *Perilla frutescens*.

8. The method according to claim 1, wherein the *perilla frutescens* extract is in a percentage from 1% to 50%, where each % is referred to the total weight of the composition.

9. The method according to claim 1 comprising an amount of the *perilla frutescens* extract from 5 mg to 500 mg.

10. The method according to claim 1, wherein the slow release component comprises a fat-soluble compound selected from fatty acids C8-C24, glycerides, fatty alcohol C8-C24, and mixture thereof.

11. The method according to claim 1, wherein the slow release component comprises at least one fat-soluble vitamin and/or at least one surfactant.

12. The method according to claim 1, wherein the slow release component further comprises cholecalciferol.

13. The method according to claim 12, comprising an amount of cholecalciferol from 1 μg to 10 μg.

14. The method according to claim 1, wherein the fast release component comprises disruptive agents, excipients diluents, adjuvants, lubricants, sweeteners or mixture thereof.

15. The method according to claim 1, wherein said composition is in the form of tablets, minitablets, capsules, or granulate.

16. Method of preventing and/or treating allergy symptoms in a subject in need thereof with a food supplement comprising a composition, said composition comprising:
- at least one slow release component comprising quercetin; and
- at least one fast release component comprising an extract from *Perilla frutescens* or a constituent thereof selected from luteolin, rosmarinic acid, apigenin, catechin, ferulic acid, caffeic acid or mixture thereof, said method comprising:
- administering to said subject an effective amount of said food supplement, wherein said allergy symptoms comprise allergic rhinitis and/or allergic conjunctivitis symptoms.

* * * * *